(12) United States Patent
Song et al.

(10) Patent No.: US 11,766,211 B2
(45) Date of Patent: Sep. 26, 2023

(54) UTERUS OCT CATHETER AND UTERUS OCT EQUIPMENT WITH PULL-BACK FUNCTION

(71) Applicant: GUANGZHOU WINSTAR MEDICAL TECHNOLOGY COMPANY LIMITED, Guangzhou (CN)

(72) Inventors: Liyan Song, Guangzhou (CN); Weiliang Liang, Guangzhou (CN); Jiangfan Pan, Guangzhou (CN); Bailing Li, Guangzhou (CN); Jun Gao, Guangzhou (CN); Zhigang Cai, Guangzhou (CN)

(73) Assignee: GUANGZHOU WINSTAR MEDICAL TECHNOLOGY COMPANY LIMITED, Guangzhou (CN)

( * ) Notice: Subject to any disclaimer, the term of this patent is extended or adjusted under 35 U.S.C. 154(b) by 610 days.

(21) Appl. No.: 16/759,318

(22) PCT Filed: Nov. 3, 2017

(86) PCT No.: PCT/CN2017/109273
§ 371 (c)(1),
(2) Date: Apr. 24, 2020

(87) PCT Pub. No.: WO2019/080158
PCT Pub. Date: May 2, 2019

(65) Prior Publication Data
US 2020/0305724 A1 Oct. 1, 2020

(30) Foreign Application Priority Data
Oct. 26, 2017 (CN) .......................... 201711013536.7

(51) Int. Cl.
 A61B 5/00 (2006.01)
 A61B 1/00 (2006.01)
(52) U.S. Cl.
 CPC .......... *A61B 5/4325* (2013.01); *A61B 1/0008* (2013.01); *A61B 1/00163* (2013.01);
 (Continued)
(58) Field of Classification Search
 None
 See application file for complete search history.

(56) References Cited

U.S. PATENT DOCUMENTS 5,047,045 A * 9/1991 Arney ................. A61M 25/104
 604/103.1
2009/0018393 A1 1/2009 Dick et al.
 (Continued)

FOREIGN PATENT DOCUMENTS

CN  202821284 U  3/2013
CN  204072038 U  1/2015
 (Continued)

OTHER PUBLICATIONS

Luer taper by Wikipedia; pub. online on May 22, 2017 at <https://en.wikipedia.org/w/index.php?title=Luer_taper&oldid=781683760> (Year: 2017).*
International Search Report issued in corresponding International application No. PCT/CN2017/109273, dated Jun. 29, 2018.
Written Opinion of the International Searching Authority for No. PCT/CN2017/109273, dated Jun. 29, 2018.

*Primary Examiner* — Christopher Koharski
*Assistant Examiner* — Michael S Kellogg

(57) ABSTRACT

The present invention provides a uterus OCT catheter, comprising: a catheter body; the catheter body comprises an outer sleeve, an OCT imaging catheter and a Luer connector; the outer sleeve is provided with an exit window; the reflecting surface of the reflecting prism in the OCT imaging catheter faces the exit window. The present invention further provides a uterus OCT equipment with pull-back function, (Continued)

comprising a pull-back device and the catheter body, the pull-back device comprises a first housing, a driving connector, a fixing sleeve and a catheter fixing tube. The invention adopts the way that the outer sleeve wraps the OCT imaging catheter to increase the overall strength and diameter; a pull-back device is adopted, the pull-back process is stable and in uniform speed, and can effectively prevent complications during human operation and damage to human tissue during pull-back process.

6 Claims, 4 Drawing Sheets

(52) U.S. Cl.
CPC .......... *A61B 5/0066* (2013.01); *A61B 5/0084* (2013.01); *A61B 5/6852* (2013.01); *A61B 2562/0242* (2013.01); *A61B 2562/225* (2013.01)

(56) References Cited

U.S. PATENT DOCUMENTS

| | | | |
|---|---|---|---|
| 2015/0196271 A1* | 7/2015 | Nair | A61B 8/085 600/468 |
| 2015/0219436 A1* | 8/2015 | Obi | G01B 9/02049 356/479 |
| 2016/0361018 A1* | 12/2016 | Courtney | A61B 8/445 |

FOREIGN PATENT DOCUMENTS

| | | |
|---|---|---|
| CN | 104977298 A | 10/2015 |
| CN | 205306957 U | 6/2016 |
| CN | 107019489 A | 8/2017 |
| WO | 2017126359 A1 | 7/2017 |

* cited by examiner

UTERUS OCT CATHETER AND UTERUS OCT EQUIPMENT WITH PULL-BACK FUNCTION

TECHNICAL FIELD

The invention relates to an OCT equipment, in particular to a uterus OCT catheter and uterus OCT equipment with pull-back function.

BACKGROUND

Optical Interference Tomography (OCT) is an optical imaging technology based on principle of weak coherent light interference, which obtain the two-dimensional or three-dimensional structure of biological tissue by detecting the back reflected or scattered signals of different tissues to the incident weak coherent light. It was first proposed by the MIT research team in 1991, because it has the advantages of fast imaging, high resolution, being non-invasive, etc., it has been widely used in the medical field.

At present, research on optical interference tomography technology at home and abroad mainly focus on OCT technology and equipment in ophthalmology, human dermatology, and cardiovascular fields, and there is no corresponding development of OCT medical equipment that can actually be used in the open luminal tracts of the human body. General OCT equipment is only suitable for imaging within a single location of tissue, however, the information represented by a single section is often limited, which is inconvenient and not conductive to medical staff to accurately diagnose the type and size of the lesion, therefore, a module that can move the scanning catheter in the axial direction must be added, thus the tissue of the open lumen of human body can be scanned and imaged at a certain axial distance. With a pull-back imaging at an axial distance, at a certain axial distance, the key information such as the shape of the tissue structure, the location and the size of the lesion can be diagnosed more clearly. Because OCT scanning technology can obtain the radial depth information of the detected tissue, the three-dimensional structure of the detected tissue can be obtained while performing axial pull-back scan imaging. OCT imaging technology does not need to add any developer, has no ionization effect and fluorescence effect, and is safer than traditional imaging technology, it is called "optical biopsy". OCT imaging technology has an optical resolution in the order of tens of microns, which is two orders of magnitude higher than X-ray and magnetic resonance imaging technology. The advantages of high resolution and non-destructive testing make OCT imaging technology extensively used in fields such as cardiovascular field, and have achieved satisfactory results. However, existing OCT equipment has two major deficiencies:

1. The direct invention of OCT technology in the cardiovascular field to the human endometrium is not entirely applicable, there are two main reasons: firstly, the OCT catheter material in the cardiovascular field is relatively soft, and the overall diameter of the catheter is small, which makes it inconvenient to operate, therefore, it is not suitable for the examination of the uterine cavity; secondly, during the examination of the endometrium, it is inevitable that the OCT catheter will closely adhere to the endometrial wall, which will destroy the morphological characteristics of the endometrial mucosal epithelium, and resulting in non-compliance with the inspection requirements.

2. The present OCT axial pull-back scanning modules are all adopt solutions that the entire OCT catheter is pulled back along the axial direction during scanning, the solution has the following disadvantages: firstly, the overall withdrawal movement of the OCT catheter is easily to cause frictional damage to the lumen mucosa of the patient's body; secondly, the overall withdrawal movement of the OCT catheter is prone to jitter, which leads to distortion or deformation of the reconstructed image; thirdly, when the overall withdrawal movement of the OCT catheter rubs against the surface of the luminal tract of the patient, it is easy to cause the secondary discomfort for the patient, which in turn leads to a decrease in the patient's treatment coordination and the corresponding problems caused thereby.

Therefore, there is imperative that a completely new OCT device that can solve the above two problems.

SUMMARY

In order to overcome the deficiencies of the prior art, the object of the present invention is to provide a uterus OCT catheter and uterus OCT equipment with pull-back function. The invention adopts the way that the outer sleeve wraps the OCT imaging catheter to increase the overall strength and diameter; At the same time, a pull-back device is adopted, and the pull-back process is stable and in uniform speed, and can effectively prevent complications during human operation and damage to human tissue during pull-back process.

The present invention provides a uterus OCT catheter, comprising: a catheter body; the catheter body comprises an outer sleeve, an OCT imaging catheter and a Luer connector; the outer sleeve is sleeved outside the OCT imaging catheter; and the Luer connector is used for fixedly connecting the outer sleeve and the OCT imaging catheter; the outer sleeve is provided with an exit window; the reflecting surface of the reflecting prism in the OCT imaging catheter faces the exit window.

Further, the Luer connector comprises a female Luer connector and a male Luer connector; the OCT imaging catheter is fixedly connected with the Luer connector; the open end of the outer sleeve is fixedly connected with the male Luer connector; the female Luer connector is fixedly connected with the male Luer connector.

Further, the female Luer connector and the male Luer connector are connected by a thread.

Further, the shape of the exit window is ring shape or circular arc shape or rectangle shape.

Further, the outer sleeve is made of a high-density polyethylene material; the shape of the closed end of the outer sleeve is solid round head shape.

A uterus OCT equipment with pull-back function, comprising a pull-back device, and the catheter body; the pull-back device comprises a first housing, a driving connector, a fixing sleeve and a catheter fixing tube; one end of the catheter fixing tube is fixed to the driving connector; the driving connector is fixedly connected to the fixing sleeve; the driving connector and the fixing sleeve are installed inside the first housing; and the catheter fixing tube is sequentially through the fixing sleeve and the first housing, the other end of the catheter fixing sleeve is fixedly connected to the Luer connector; the driving connector connects a rotary driver and a linear driver, the rotary driver drives the driving connector and drives the catheter body to rotate around the axis; the liner driver drives the driving connector and drives the catheter body to reciprocate in the axial direction.

Further, the pull-back device further comprises a second housing; the first housing is provided with a first locating hole, the second housing is provided with a second locating hole; the catheter fixing tube is located through the first locating hole and the second locating hole.

Further, the pull-back device further comprises a pressure balancer; the pressure balancer is installed inside the balance cavity of the second housing; the second housing is provided with a gas channel communicating with the external space and the balance cavity respectively.

Further, pull-back device further comprises a sealing device; the sealing device separately seals the pressure balancer and the balance cavity, the catheter fixing tube and the second housing; the sealing device is specifically sealing rings.

Further, the pull-back device further comprises a stop pin; the fixing sleeve is provide with a stop plate; the stop plate and the stepped surface of the fixing sleeve form a position limiting part; the stop pin is inserted into position limiting part, the stop pin is installed in the first mounting hole of the side wall of the first housing.

Further, the driving connector and the fixing sleeve are fixedly connected by a fixing pin; the driving connector is provided with a concave part; the fixing pin touches against the concave part, and at the same time, the fixing pin is inserted into and connected to the second mounting hole of the side wall of the fixing sleeve.

Compared with the prior art, the beneficial effects of the present invention are:

The present invention provides a uterus OCT catheter, comprising: a catheter body; the catheter body comprises an outer sleeve, an OCT imaging catheter and a Luer connector; the outer sleeve is sleeved outside the OCT imaging catheter; and the Luer connector is used for fixedly connecting the outer sleeve and the OCT imaging catheter; the outer sleeve is provided with an exit window; the reflecting surface of the reflecting prism in the OCT imaging catheter faces the exit window. The present invention also relates to a uterus OCT equipment with pull-back function, comprising a pull-back device, and the catheter body; the pull-back device comprises a first housing, a driving connector, a fixing sleeve and a catheter fixing tube; one end of the catheter fixing tube is fixed to the driving connector; the driving connector is fixedly connected to the fixing sleeve; the driving connector and the fixing sleeve are installed inside the first housing; and the catheter fixing tube is sequentially through the fixing sleeve and the first housing, the other end of the catheter fixing sleeve is fixedly connected to the Luer connector; the driving connector connects a rotary driver and a linear driver, the rotary driver drives the driving connector and drives the catheter body to rotate around the axis; the liner driver drives the driving connector and drives the catheter body to reciprocate in the axial direction. The invention adopts the way that the outer sleeve wraps the OCT imaging catheter to increase the overall strength and diameter; At the same time, a pull-back device is adopted, and the pull-back process is stable and in uniform speed, and can effectively prevent complications during human operation and damage to human tissue during pull-back process. The invention has strong practicability, ingenious design and easy promotion.

The above description is only an overview of the technical solution relating of the present invention. In order to be able to understand the technical means of the present invention more clearly and to implement it in accordance with the contents of the description, the following is a detailed description of preferred embodiments of the present invention and the accompanying drawings as follows. The specific embodiments of the present invention are given in detail by the following examples and their drawings.

BRIEF DESCRIPTION OF THE DRAWINGS

The drawings described herein are used to provide a further understanding of the present invention and form a part of the present invention, the proprietary embodiments of the present invention and their descriptions are used to explain the present invention and do not constitute an undue limitation of the present invention. In the drawing.

Figure 1:
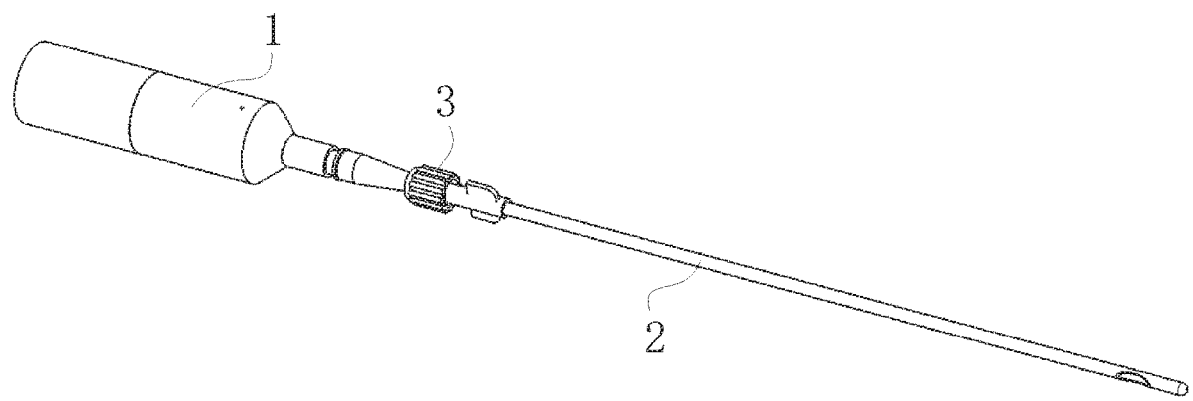
FIG. 1 is a schematic diagram of the overall structure of a uterus OCT equipment with pull-back function of the present invention.

In the FIGs: pull-back device 1, first housing 11, first locating hole 111, first mounting hole 112, second housing 12, second locating hole 121, driving connector 13, fixing sleeve 14, second mounting hole 141, stop plate 142, pressure balancer 15, catheter fixing tube 16, sealing device 17, stop pin 18, fixing pin 181, guiding sleeve 19, catheter body 2, outer sleeve 21, exit window 211, closed end 212, OCT imaging catheter 22, light guiding tube 23, reflecting prism 24, exit beam 25, Luer connector 3, female Luer connector 31, male Luer connector 32.

DESCRIPTION OF EMBODIMENTS

The present invention will be further described below with reference to the drawings and specific implementations. It should be noted that, under the premise of no conflict, any combination of the embodiments described below or each technical feature can be arbitrarily combined to form a new embodiment.

Figure 7:
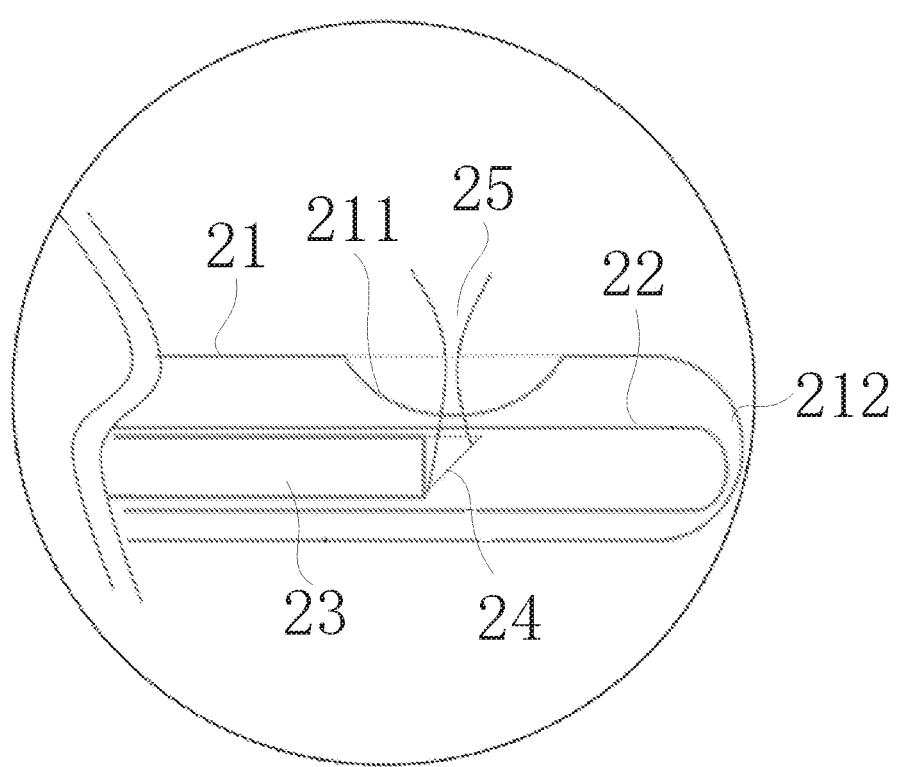
FIG. 7 is a partial cross-sectional diagram of the catheter body of the present invention.

A uterus OCT catheter, as shown in FIG. 1, FIG. 7, comprising a catheter body 2; the catheter body 2 comprises an outer sleeve 21, an OCT imaging catheter 22 and a Luer connector 3; the outer sleeve 21 is sleeved outside the OCT imaging catheter 22; and the Luer connector 3 is used for fixedly connecting the outer sleeve 21 and the OCT imaging catheter 22; the outer sleeve 21 is provided with an exit window 211; the reflecting surface of the reflecting prism 24 in the OCT imaging catheter 22 faces the exit window 211.

Figure 3:
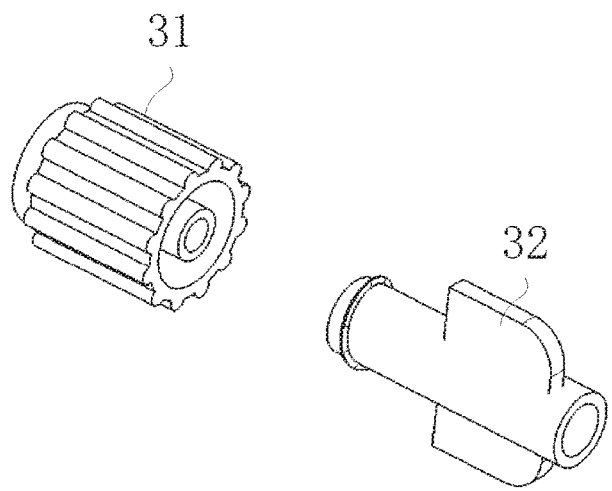
FIG. 3 is a schematic diagram of the structure of the Luer connector of the present invention.

In one embodiment, as shown in FIG. 3, the Luer connector 3 comprises a female Luer connector 31 and a male Luer connector 32; the OCT imaging catheter 22 is fixedly connected with the female Luer connector 31; the open end of the outer sleeve 21 is fixedly connected with the male Luer connector 32; the female Luer connector 31 is fixedly connected with the male Luer connector 32. The OCT imaging catheter 22 and the outer sleeve 21 are fixedly and positioned at the same time by the Luer connector 3, at this time, the OCT imaging catheter 22 is located inside the outer sleeve 21. Specifically, the female Luer connector 31 and the male Luer connector 32 are connected by thread; as shown in FIG. 3, the male Luer connector 32 is provided with two side-wings, and by rotating the two side-wings, the thread fit of the female Luer connector 31 and the male Luer connector 32 is achieved.

In one embodiment, the shape of the exit window 211 is ring shape or circular arc shape or rectangle shape. As shown in FIG. 7, the shape of the exit window 211 is circular arc; the outer sleeve 21 is made of a medical high-density polyethylene material with moderate hardness which improves the overall strength while increasing the overall diameter. The thickness of the outer sleeve 21 is related to the detection depth of the uterus OCT catheter, specifically, the thickness of the outer sleeve 21 is equal to the distance the exit beam 25 from the outside of the outer nylon tube of the OCT imaging catheter 22 to the waist position of the exit beam 25, the exit beam 25 is transmitted from the light guiding tube 23 in the OCT imaging catheter 22. Specifically, the exit window 211 is coaxial with the center of the exit beam 25 of the light guiding tube 23 to ensure that the OCT equipment has an accurate focal length and accurate measurement. In particular, the shape of the closed end 212 of the outer sleeve 21 is solid round head shape, which ensures that it will not cause scratches when protruding into the human body.

Figure 2:
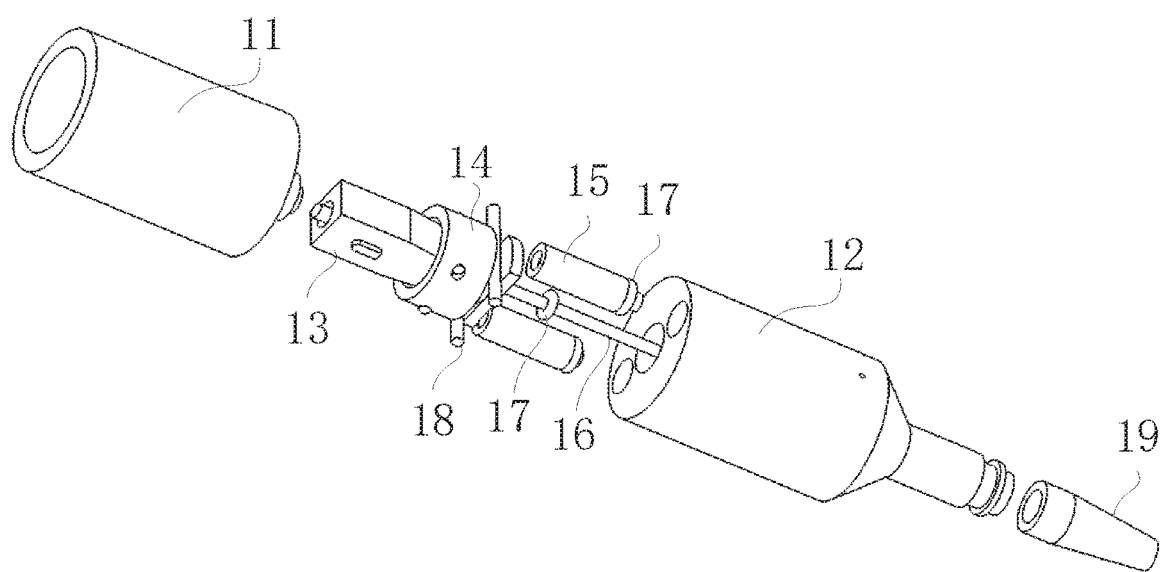
FIG. 2 is a schematic diagram 1 of the exploded structure of the pull-back device of the present invention.

A uterus OCT equipment with pull-back function, as shown in FIG. 1, comprising a pull-back device 1 and the catheter body 2; as shown in FIG. 2, the pull-back device 1 comprises a first housing 11, a driving connector 13, a fixing sleeve 14 and a catheter fixing tube 16; one end of the catheter fixing tube 16 is fixed to the driving connector 13; the driving connector 13 is fixedly connected to the fixing sleeve 14; the driving connector 13 and the fixing sleeve 14 are installed inside the first housing 11; and the catheter fixing tube 16 is sequentially through the fixing sleeve 14 and the first housing 11, the other end of the catheter fixing tube 16 is fixedly connected to the Luer connector 3; the driving connector 13 connects a rotary driver and a linear driver, the rotary driver drives the driving connector 13 and drives the catheter body 2 to rotate around the axis; the liner driver drives the driving connector 13 and drives the catheter body 2 to reciprocate in the axial direction.

Figure 4:
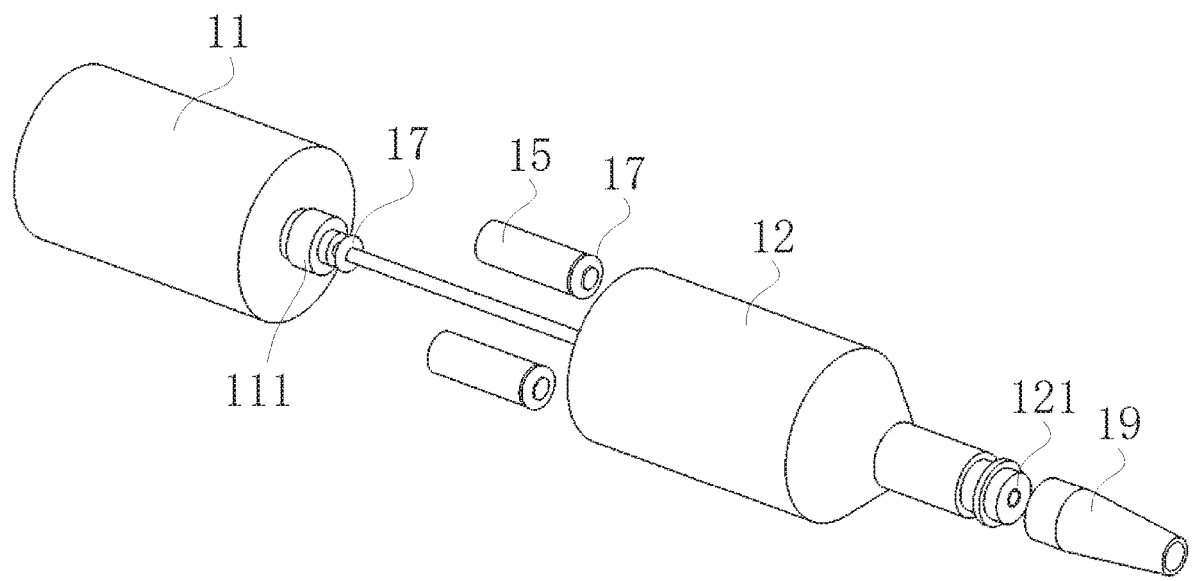
FIG. 4 is a schematic diagram 2 of the exploded structure of the pull-back device of the present invention.
Figure 5:
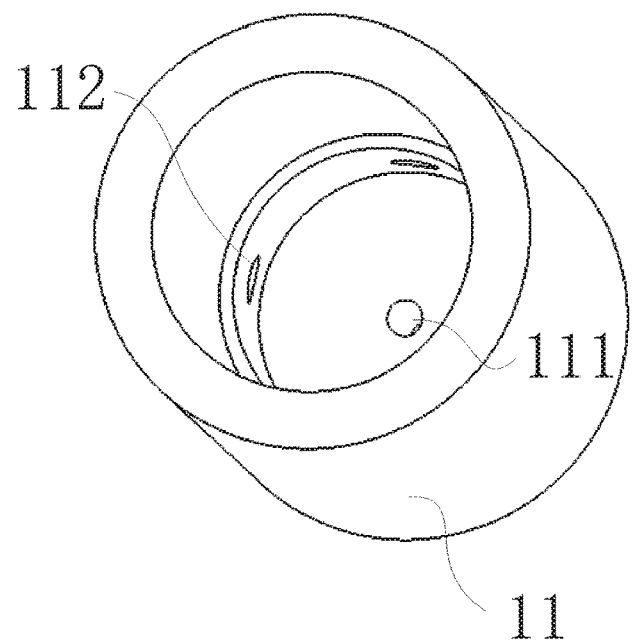
FIG. 5 is a schematic diagram of the structure of the first housing of the present invention.
Figure 6:
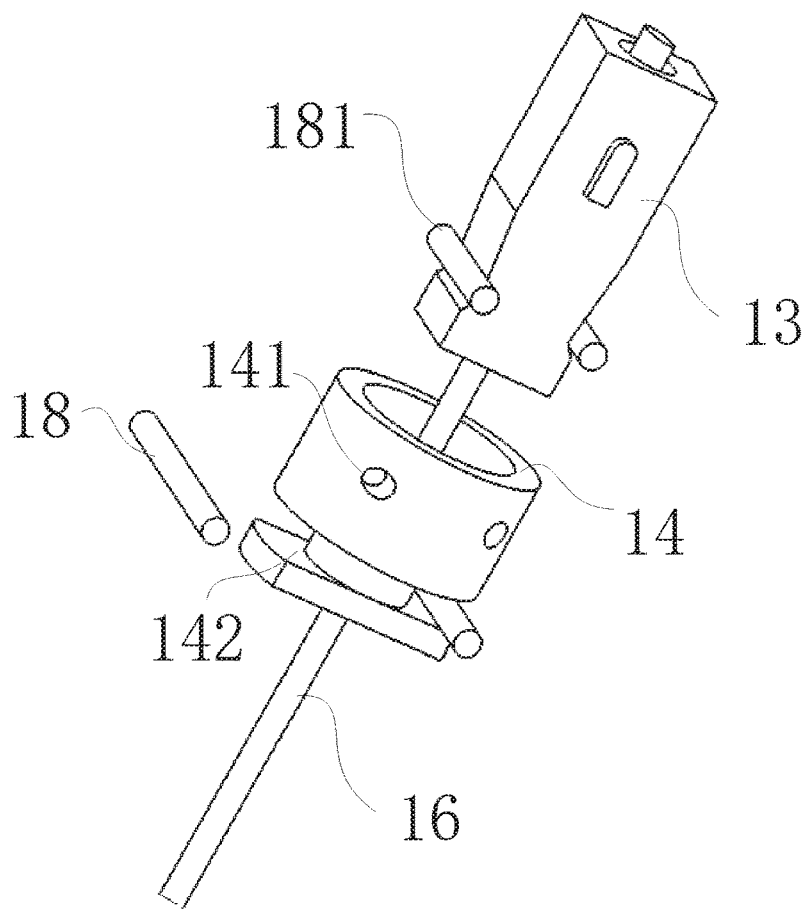
FIG. 6 is a schematic diagram of a partial structure of a pull-back device of the present invention.

In one embodiment, as shown in FIG. 2, FIG. 4, the pull-back device 1 further comprises a second housing 12, the first housing 11 is provided with a first locating hole 111, the second housing 12 is provided with a second locating hole 121; the catheter fixing tube 16 is located through the first locating hole 111 and the second locating hole 121, ensure that the catheter fixing tube 16 is coaxial with the first housing 11 and the second housing 12, so that the catheter fixing tube 16 can smoothly extend out of the guiding sleeve 19 and connect to the female Luer connector 31.

In one embodiment, as shown in FIG. 2, FIG. 4, the pull-back device 1 further comprises a pressure balancer 15; the pressure balancer 15 is installed inside the balance cavity of the second housing 12; the second housing 12 is provided with a gas channel communicating with the external space and the balance cavity respectively; specifically, two pressure balancer 15 are installed in the balance cavity of the second housing 12, the balance of pressure inside and outside the equipment can be achieved by the pressure balancer 15 being able to move back and forth; in particular, the pull-back device 1 further comprises a sealing device 17; the sealing device 17 separately seals the pressure balancer 15 and the balance cavity, the catheter fixing tube 16 and the second housing 12; the sealing device 17 is specifically sealing rings.

In one embodiment, as shown in FIG. 2, FIG. 4-6, the pull-back device 1 further comprises a stop pin 18; the fixing sleeve 14 is provide with a stop plate 142; the stop plate 142 and the stepped surface of the fixing sleeve 14 form a position limiting part; the stop pin 18 is inserted into position limiting part, the stop pin 18 is installed in the first mounting hole 112 of the side wall of the first housing 11. Specifically, the driving connector 13 is provided with a concave part; the fixing pin 181 touches against the concave part, and at the same time, the fixing pin 181 is inserted into and connected to the second mounting hole 141 of the side wall of the fixing sleeve 14. In particular, the stop pin 18 can be a spring latch or a movable latch.

when using it, when the uterine OCT catheter needs to be pushed forward or be pulled back, the stop pin 18 is not inserted in the position limiting part, at this time, the fixing sleeve 14 is unlocked axially; the driving connector 13 is driven by the linear driver (such as a lead screw or linear motor) to drive the catheter body 2 to reciprocate in the axial direction; when the catheter body 2 moves to the image acquisition position, at this time, the stop pin 18 is inserted into the position limiting part, and the fixing sleeve 14 is axially locked, the driving connector 13 and the fixing sleeve 14 cannot move axially in the first housing 11, the driving connector 13 is driven by a rotary driver (such as a rotary electric machine or a rotary motor), which drives the catheter body 2 to rotate around its own axis, and the exit beam 25 passes through the exit window 211 to achieve 360° rotation scanning.

The present invention provides a uterus OCT catheter, comprising: a catheter body 2; the catheter body 2 comprises an outer sleeve 21, an OCT imaging catheter 22 and a Luer connector 3; the outer sleeve 21 is sleeved outside the OCT imaging catheter 22; and the Luer connector 3 is used for fixedly connecting the outer sleeve 21 and the OCT imaging catheter 22; the outer sleeve 21 is provided with an exit window 211; the reflecting surface of the reflecting prism 24 in the OCT imaging catheter 22 faces the exit window 211. The present invention also relates to a uterus OCT equipment with pull-back function, comprising a pull-back device 1, and the catheter body 2; the pull-back device 1 comprises a first housing 11, a driving connector 13, a fixing sleeve 14 and a catheter fixing tube 16; one end of the catheter fixing tube 16 is fixed to the driving connector 13; the driving connector 13 is fixedly connected to the fixing sleeve 14; the driving connector 13 and the fixing sleeve 14 are installed inside the first housing 11; and the catheter fixing tube 16 is sequentially through the fixing sleeve 14 and the first housing 11, the other end of the catheter fixing sleeve 14 is fixedly connected to the Luer connector 3; the driving connector 13 connects a rotary driver and a linear driver, the rotary driver drives the driving connector 13 and drives the catheter body 2 to rotate around the axis; the liner driver drives the driving connector 13 and drives the catheter body 2 to reciprocate in the axial direction. The invention adopts the way that the outer sleeve 21 wraps the OCT imaging catheter 22 to increase the overall strength and diameter; At the same time, a pull-back device 1 (ie, backward moving device or draw-back device) is adopted, and the pull-back process is stable and in uniform speed, and can effectively prevent complications during human operation and damage to human tissue during pull-back process. The invention has strong practicability, ingenious design and easy promotion.

The above are only preferred embodiments of the present invention, and do not limit the present invention in any form; any person of ordinary skill in the industry can smoothly implement the present invention as shown in the accompanying drawings of the description and above. However, those skilled in the art without departing from the scope of the technical solution of the present invention, using the technical content disclosed above to make some equivalent changes, modifications and evolutions, are equivalent embodiments of the invention. At the same time, any changes, modifications and evolutions made to the above embodiments based on the essential technology of the present invention still fall within the protection scope of the technical solution of the present invention.

What is claimed is:

1. A uterus OCT equipment with pull-back function, comprising a pull-back device, and a catheter body; the catheter body comprises an outer sleeve, an OCT imaging catheter and a Luer connector; the outer sleeve is sleeved on the OCT imaging catheter; and the Luer connector is used for fixedly connecting the outer sleeve and the OCT imaging catheter;

the pull-back device comprises a first housing, a driving connector, a fixing sleeve and a catheter fixing tube; a first end of the catheter fixing tube is fixed to the driving connector; the driving connector is fixedly connected to the fixing sleeve; the driving connector and the fixing sleeve are installed inside the first housing; and the catheter fixing tube passes through the fixing sleeve and the first housing in sequence, a second end of the catheter fixing tube is fixedly inserted into the Luer connector; the driving connector connects a rotary driver and a linear driver, the rotary driver is configured to drive the driving connector to rotate, so the catheter body is driven to rotate around an axis of the catheter body; the liner driver is configured to drive the driving connector to move, so the catheter body is driven to reciprocate in an axial direction of the catheter body.

2. The uterus OCT equipment with pull-back function of claim 1, wherein the pull-back device further comprises a second housing; the first housing is provided with a first locating hole, the second housing is provided with a second locating hole; the catheter fixing tube is located through the first locating hole and the second locating hole.

3. The uterus OCT equipment with pull-back function of claim 2, wherein the pull-back device further comprises a pressure balancer; the pressure balancer is installed inside a balance cavity of the second housing; the second housing is provided with a gas channel communicating with an external space and the balance cavity respectively.

4. The uterus OCT equipment with pull-back function of claim 3, wherein the pull-back device further comprises a sealing device; the sealing device separately seals the pressure balancer and the balance cavity, the catheter fixing tube and the second housing; the sealing device comprises sealing rings.

5. The uterus OCT equipment with pull-back function of claim 1, wherein the pull-back device further comprises a stop pin; the fixing sleeve is provide with a stop plate; the stop plate and a stepped surface of the fixing sleeve form a position limiting part; the stop pin is inserted into the position limiting part, the stop pin is installed in a first mounting hole of a side wall of the first housing.

6. The uterus OCT equipment with pull-back function of claim 1, wherein the driving connector and the fixing sleeve are fixedly connected by a fixing pin; the driving connector is provided with a concave part; the fixing pin contacts the concave part, and the fixing pin is inserted into and connected to a second mounting hole of a side wall of the fixing sleeve.

* * * * *